(12) United States Patent
Ray et al.

(10) Patent No.: US 6,991,814 B2
(45) Date of Patent: Jan. 31, 2006

(54) HERBAL MEDICAMENTS FOR THE TREATMENT OF NEUROCEREBROVASCULAR DISORDERS

(75) Inventors: Madhur Ray, Uttar Pradesh (IN); Raghwendra Pal, Uttar Pradesh (IN); Satyawan Singh, Uttar Pradesh (IN); Nandoo Mal Khanna, Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 26 days.

(21) Appl. No.: 10/319,373

(22) Filed: Dec. 13, 2002

(65) Prior Publication Data

US 2004/0033277 A1 Feb. 19, 2004

Related U.S. Application Data

(60) Provisional application No. 60/340,165, filed on Dec. 14, 2001.

(51) Int. Cl.
*A61K 35/78* (2006.01)

(52) U.S. Cl. .................................................. 424/725
(58) Field of Classification Search ................ 424/725, 424/195.1
See application file for complete search history.

(56) References Cited

PUBLICATIONS

Revilla et al. Comparison of Several Procedures Used for the Extraction of Anthocyanins From Red Grapes; J. Agric. Food. Chem.(1998) 46, pp. 4592–4597.*

Krishnamurthy et al. Oil and Oleoresin of Turmeric; Tropical Science (1976), 18 (1) pp. 37–45.*

Jangde et al. Anti–Inflammatory Activity of Extracts of *Curcuma Aromatica* SAISB; Indian Vet. J. (1998) 7 No. 1, pp. 76–77.*

Wuthi–udomlert et al. Antifungal Activity of *Curcuma longa* Grown in Thailand; Southeast Asian Journal of Tropical Medicine and Public Health (2000) 31, Suppl. 1, pp. 178–82.*

Choudhury et al. Volatile Constituents of the Aerial and Underground Parts of *Curcuma aromatica* SILISB From India; J. Essent. Oil. Res (1996), 8 (6), pp. 633–638.*

* cited by examiner

*Primary Examiner*—Patricia Leith
(74) *Attorney, Agent, or Firm*—Ladas and Parry LLP

(57) ABSTRACT

The present invention relates to A composition obtained from the lipid soluble extract of rhizomes and leaves of *Curcuma species* of Zingiberaceae family, useful for the treatment of neurocerebrovascular disorders, said composition comprising fraction A consisting of ar-turmerone of formula 1, and turmerone of formula 2, and/or along with fraction B consisting of curcumene and zingiberine, and/or fraction C consisting of germacrone, curcumerone, zedoarone, sedoarondiol, isozdedoaronidiol, curcumenone, and curlone, and/or pharmaceutically acceptable additives and a method of treating neurocerebrovascular disorders in animals including humans using said composition by administering therapeutically effective amount of lipid soluble extract.

8 Claims, 9 Drawing Sheets

Ischaemia　　Fraction B

HERBAL MEDICAMENTS FOR THE TREATMENT OF NEUROCEREBROVASCULAR DISORDERS

This application claims the benefit of U.S. Provisional Application No. 60/340,165 filed Dec. 14, 2001 and incorporates the same by reference.

FIELD OF THE PRESENT INVENTION

The present invention relates to the method of producing lipid soluble extract called *Curcuma* oil in high yield, from rhizomes and leaves of species of zingiberaceae family, particularly *Curcuma* species and also use of the said oil, its constituents, and novel derivatives of said constituents, for the treatment of Neurocerebrovascular disorders

BACKGROUND AND PRIOR ART REFERENCES

Neurocerebrovascular diseases like cerebrovascular infarction, stroke, ischemic attacks etc. are caused by an interruption of the blood supply resulting from disease of the arteries carrying blood to the brain.

Of the three general types of stroke, cerebral hemorrhage is caused by rupture of a blood vessel with bleeding into the brain (intra cerebral hemorrhage) or under its covering membrane, while cerebral thrombosis stems from obstruction of a cerebral blood vessel when a blood clot forms within the walls.

The clot may be caused by abnormal thickening of the blood, damage to the vessel wall from arteriosclerosis, atherosclerosis, inflammation of the arteries or inflammation of the veins.

If the blood supply is stopped completely or is reduced to less than one-fourth its normal level, softening of the brain (cerebral infarction) results, causing permanent brain damage.

Cerebral embolism is obstruction of a cerebral artery by a blood clot or a foreign body migrating from another part of the body's circulation like when a clot that has formed on the inside wall of one of the arteries in the neck travels up to the brain and blocks a major artery branch.

Trasient ischemic attacks (TIAs) are brief episodes of symptoms caused by temporary interruptions of the blood supply. Reversible ischemic neurological deficits(RINDs) are small cerebral infarction. Multiple cerebral infarction can lead to permanent confusion and memory loss. Ischemic stroke is a medical emergency. After TIAs or stroke occur, treatment may be surgical or medical. Surgery may be needed in some cases to remove any blockage of blood vessels going to the brain.

Medication can prevent the formation of blood clots on the atherosclerotic plaques within the vessel wall. Brain swelling commonly accompanies brain infarction or hemorrhage. No satisfactory treatment is available.

Currently used drugs in perpheral vascular and cerebral disorders include ergot alkaloids, aspirin, anti-coagulants etc. The latter are used following strokes to prevent further cerebrovascular incidents but their use is contraindicated if the stroke was the result of hemorrhage.

The use of TICLOPIDINE, a highly effective antiplatelet agent to treat stroke cases is restricted in its long term use due to its adverse side-effects. Tissue plasminogen activator (t-PA) used to treat clots in the coronary arteries (acute heart attack), is a natural clot dissolving substance produced by the body which can blow open a blood clot in the brain that causes the acute ischemic brain damage characteristic of a stroke. While t-PA can dissolve the blood clot that causes a blood vessel blockage, there are other complications which occur during ischemic stroke which must be addressed if permanent brain damage is to be prevented. It is critically important to have nitric oxide (NO) and superoxide scavengers in the blood stream when t-PA is administered to reduce the free radical damage that will occur when the blood flow is restricted and even more when the flow is resumed.

Nitric oxide(NO) and superoxides inflict damage on important biomolecules and their increased production has been implicated in human diseases like cerebro-, cardiovascular, inflammatory, neurological dysfunctions and cancer etc.[Onoda M., Inano H., Nitrc oxide: Biology and Chemistry, 4, (5), 505–515 (2000)].

Most strokes culminate in a core area of cell death (infarction) and the blood flow is so drastically reduced that the cells usually can not recover. Brain cells die as a result of the actions: calcium activated proteases (enzymes which digest cell proteins), lipases (enzymes which digest cell membranes) and free radicals formed as a result of the ischemic cascade. Without neuroprotective agents, nerve cells may be irreversibly damaged within several minutes. Any disruption of blood flow to the brain causes massive free radical damage that induces much of the reperfusion injury to brain cells, typical of strokes. When blood flow is interrupted and subsequently restored (reperfused), tissues release iron that acts as a catalyst for the formation of free radicals that often permanently damage brain cells. Protecting brain cells from injury caused by blood flow disruption, therefore, is of prime importance. If an ischemic stroke is happening, the use of large quantities of anti-oxidants like melatonin, vitamins and herbs like *Ginkgo biloba* have been suggested to provide some benefit. Magnesium in an oral dose of 1500 mg. is a safe nutrient to relieve an arterial spasm, a common problem in thrombotic strokes.

The ancient Indian system of medicine-Ayurveda—is concerned with the prevention, diagnosis and cure of disease. The word "dis-ease"—a right translation of illness is viewed as a dysfunction of the whole body and is attributed to the circulation and transformation of ubiquitous humoral fluids.

Most of the Ayurvedic drugs are products of high repute which act on a number of dysfunctions of the body involving various organs and aim at preventing problems or restoring a normal situation, and try to recover the patient completely. Evolved over a long period of time and experimentation, they are the results of a particular combination of certain fundamental elements which determine their properties which in turn are responsible for the chemical, biological or therapeutic effects of those substances. There is no substance when correctly prepared which can not be used as remedy.

Ayurveda describes a number of beneficial effects of rhizomes and leaves of various species belonging to zingiberaceae family, especially those of *Curcuma longa* L.syn. *Curcuma domestica* Valeton, rhizomes and leaves popularly known as Turmeric or Haldi. Prominent among these are the anti-bacterial, antifungal wound healing and the anti-inflammatory actions which enabled turmeric paste to be used as a house hold remedy to treat wounds and inflammation.

In recent years, its constituents-Curcumin and other curcuminoids have been found to exhibit besides these activities, choleretic, cholagogic, anti-oxidant, anti-cancer, inhibition of leukotriene biosynthesis, 5-lipoxygenase, cyclo-oxygenase, lipid peroxidation, superoxide and nitric oxide (NO) scavenging effects. Turmeric—a highly reputed herb in Indian system of medicine-Ayurveda-is the rhizome of *Curcuma longa* L.Syn. *Curcuma domestica* Valeton (Fam. Zingiberaceae) which grows abundantly in India. It has long been used as a spice and a colouring agent in food as well as a naturally occurring medicine. Its powder or extracts are recommended to treat wounds and inflammation.

A major constituent Curcumin was developed as an anti-inflammatory agent [Srimal R. C., Khanna N. M., Dhawan B. N., Ind. J. Pharmacol., 3, 10 (1971)]. Other therapeutic properties of Curcumin, various curcuminoids and some other constituents of *Curcuma* species include anti-bacterial, anti-fungal [Schraufstatter F., Brent H., Nature, 164,456(1949), Arch. Dermatol.u.Syphilis, 188,250 (1949); Lutomski. J., KedziaB., Debska W, Planta Med., 26, 9 (1974); Rao B. G. N., Joseph P., Reichst, Aromen Koerperflegem, 21, 405–406(1971); Swada T., Yamahara J., Shimazu S., Ohta T., Shoyakugaku Zasshi, 2, 11–16(191), Prasad C. R., Sirsi M., J. Sci. Ind. Res., C. 15, 239–41 (1957); Schraufstatter E., Deutsh. S. Z. Naturforsch. 4, 276 (1949); Chopra R. N., Gupta J. C., Chopra G. S., Ind. J. Med. Res., 29, 769–72 (1941)], anti-oxidant [Ramaswamy T. S., Baneijee B. N., Ann. Biochem. Exp. Med., 8, 55 (1948); Chipault .J. R., Mizuno G. R., Lundberg W. O., Food Res., 10, 209, (1956)]; inhibition of lipid per-Oxidation [Sharma S. C., Mukhtar H., Sharma S. K., Krishnamurty C. R., Biochem. Biopharmacol., 21, 1210–14 (1972); Zu S., Tang. X. Lin Y., Zhougcuoyev., 22, 264–5(1991); Sharma O. P., Biochem. Biopharmacol. 25, 1811(1976)]; active oxygen species scavenging and prevention of increased free radical formation by Curcumin in the body [Tennesen H. H., Inter. J. Pharmacol., 50, 67–69(1989), Kunchandy E., Rao M. N. A., Inter. J. Pharmacol., 58, 237 (1990)]; inhibitory activity for iNOS induction by lipopolysacchande in the mammary gland and scavenging activity for NO radicals by Curcumin, [Onoda M., Inano H., Nitric Oxide: Biology and Chemistry, 4, 505–515 (2000)], anti-inflammatory [Arora R. B., Basu N., Kapoor V., Jain A., Proc. Second Indo Soviet Symposium on Natural Products, New Delhi, 1970, p. 170., Ind. J. Med. Res., 59, 10 (1971); Mukhopadhya A., Basu N., Ghatak N., Singh K. P., Gujral P. D., Proc. Int. Union of Physiol. Sci., 11, 241(1974); Ghatak N. N., Basu N., Ind. J. Exp. Biol., 10, 235 (1972), Chandra D., Gupta S. S., Ind. J. Med. Res., 60, 138–142 (1972)]; anti-cancer [Soudamini K. K., Kuttan R., J. Ethnopharmacol. 27, 227 (1989); Kuttan R. Bhanumatty P., Nirmala K., George M. C., Cancer Lett., 29, 197 (1985)]; antioxidant and antitumor promotor which induces apoptosis in human leukemia cells [Rao M. L., Huang T. S., Lin J. K., Biochem. Biophysic. Acta, 1817, 98–100(1996)], inhibition of cell growth in chinese hamster ovary cell culture and cytotoxicity to lymphocytes and Dalton's lymphomaCells., [Cancer Lett. (Ireland), 29, 197 (1985) via Chem. Abstr. 104, 61654$^d$ (1986)], tumor protecting activity in mouse skin carcinogenesis induced by 7, 12-dimethyl benz (a) anthracene [Kyoto-Furiton Doigaku Zasshi, 96, 725 (1987)-via Chem. Abstr., 107, 211555$^a$ (1987)], inhibition of HIV protease [Suz Luz, Craik C. S., Oritz T., Montanello P. R., Proc. 205, ACS National Meeting, Denver, Colo., 28 March–2 April, Amer. Chem. Soc. Med. Chem. Div. (1993), Take Y., Inoyya H., Nakamura S., Alauddin H. S., Kuba A., J. Antibiot., 42, 107–118 (1989)], inhibition of lipoxygenase, cyclooxygenase [Tennesen. H. H., Int. J Pharmacol., 50., 67 (1989), inhibition of ADP-epinephrine and collagen induced platelet aggregation, [Srivastava R., Puri V., Srimal R. C., Dhawn B. N.; Arznei Forsch., 36, 715–717(1986)]; protection against thrombotic challenge [Srivastava R., Dixit M., Srimal R. C., Dhawan B. N., Thromb. Res., 40, 413–17(1985)]; reduction in ratio of total cholesterol/phospholipids in hyperlipidemic rats and elivated HDL-cholesterol and total cholesterol ratio [Ind. J. Physiol. Pharmacol., 32, 299 (1988)]; anticoagulent activity [Chem. Pharm. Bull., 33, 1499 (1985)]; inhibition of platelet aggregation, metabolic disorders and hyperlipidemia [Lin Y., U.S. Pat. No. 4,842,849; Chem. Abstr., 111, 160200 (1984); Khanna N. M., Sarin J. P. S., Singh S., Pal R., Seth R. K., Nitya Nand S., Indian Patent 162441(1984)]; which makes it useful to prevent cardiovascular disorders like ischemic heart attacks, myocardial infarction etc. In Indo-China region, *Curcuma* extracts are given at parturition on account of their anticoagulent action. Ethyl p-methoxy cinnamate isolated from *Curcuma* rhizomes essential oil exhibit antifungal activity [Herba Hung., 28, 95(1989), via Chem. Abstr. 111, 191496j (1989)], while furanogermenone and (4S,5S) (+) germacrone 4,5-epoxide also isolated from *Curcuma* rhizomes essential oil exhibits anti-inflammatory and preventive effect against stress ulceration [Yakugaku Zasshi, 106, 1137 (1986), Chem. Abstr. 106, 95935c (1987); Zhongyao Tungbto, 10, 134 (1983), Chem. Abstr. 103, 115886d(1985)]. The other reputed herb from Zingiberaceae family, *Zingiber officinale* Rosch, exhibits preventive effects in heart attack or stroke [Srivastava K. C., Prostaglandins Leukotrienes and Medicines, 13,227–235(1964)].

OBJECTS OF THE PRESENT INVENTION

The main object of the present invention is to use the lipid soluble extract from rhizomes and leaves of Curcuma species, which belong to zingiberaceae family for the treatment of Neurocerebrovascular disorder.

Another object of the present invention is to develop a method to produce lipid soluble extract in high yield from rhizomes and leaves of *Curcuma* species, which belong to zingiberaceae family.

Yet another object of the present invention is to separate individual components from the *Curcuma* oil.

Still another object of the present invention is to develop analogs of the said constituents of the *Curcuma* oil.

Still another object of the present invention is to detect the Neurocerebrovascular disorders of the said analogs.

SUMMARY OF THE PRESENT INVENTION

The present invention relates to the method of producing lipid soluble extract called *Curcuma* oil in high yield. The source of said oil is rhizomes and leaves of species of zingiberaceae family. The particularly species of the said family used to produce said oil is *Curcuma* species. The said oil is used for the treatment of Neurocerebrovascular disorders. The novel analogs of the constituents of said oil are developed and are also found to have use in the treatment of Neurocerebrovascular disorder.

DETAILED DESCRIPTION OF THE INVENTION

Accordingly the present invention relates to an improved method of obtaining high yields of the lipid soluble extract called *Curcuma* oil and its constituents from rhizomes and leaves of species of Zingiberaceae family particularly *Curcuma* species.

A composition obtained from the lipid soluble extract of rhizomes and leaves of *Curcuma* species of Zingiberaceae family, useful for the treatment of neurocerebrovascular disorders, said composition comprising fraction A consisting of ar-turmerone of formula 1, and turmerone of formula 2, and/or along with fraction B consisting of curcumene and zingiberine, and/or fraction C consisting of germacrone, curcumerone, zedoarone, sedoaronidiol, isozdedoaronidiol, and curlone, and/or pharmaceutically acceptable additives. (Hereinafter "composition obtained from the lipid soluble extract of rhizomes and leaves of *Curcuma* species of Zingaberaceae.")

A composition obtained from the lipid soluble extract of rhizomes and leaves of *Curcuma* species of Zingaberaceae, wherein the *curcuma* species is *Curcuma domestica* Valeton.

A composition obtained from the lipid soluble extract of rhizomes and leaves of *Curcuma* species of Zingaberaceae, wherein the ratio of fraction A, fraction B, and fraction C is ranging between 1 to 3:1 to 3:1 to 3.

A composition obtained from the lipid soluble extract of rhizomes and leaves of *Curcuma* species of Zingaberaceae, wherein additives are selected from a group comprising melatonin, antioxidants, calcium channel antagonists, tissue plasminogen activator (t-PA0, and cell membrane stabilizing agents.

A composition obtained from the lipid soluble extract of rhizomes and leaves of *Curcuma* species of Zingaberaceae, wherein said composition inhibits nitric oxide syrithase (NOS) overproduction, prevention calcium overload in neurons, and scavenging free radicals.

A composition obtained from the lipid soluble extract of rhizomes and leaves of *Curcuma* species of Zingaberaceae, wherein said composition is used to treat cerebrovascular disorders which are selected from a group comprising iscaemia, stroke, post-stroke injury, hemorrhage, reperfusion injury, thrombosis, vasoconstriction, nitric oxide-induced free radical oxidative damage, infraction, inflammation, and Alxheimer's disease.

A composition obtained from the lipid soluble extract of rhizomes and leaves of *Curcuma* species of Zingaberaceae, wherein fraction A of the composition is most effective.

A composition obtained from the lipid soluble extract of rhizomes and leaves of *Curcuma* species of Zingaberaceae, wherein said disorders are treated using the composition in a form of various delivery systems selected from a group comprising tablets, capsules, suppository, beads, and aerosols.

In still another embodiment of the present invention, there is provided an improved method for obtaining high yield lipid soluble extract and its subsequent fractions comprising fraction A consisting of ar-turmerone of formula 1, and turmerone of formula 2, fraction B consisting of curcumene and zingiberine, and fraction C consisting of germacrone, curcumerone, zedoarone, sedoarondiol, isozdedoaronidiol, and curlone, from rhizomes and leaves of *Curcuma* species Zingiberaceae family, said method comprising the steps of:

powdering the rhizomes and leaves of the *curcuma* species in fine particles form, extracting the powder with polar organic solvent under continuous stirring or sonication for about 24 hours at room temperature, repeating step (b) two to five times, removing solvent by distillation under reduced pressure and below about 45° C. to obtain residual concentrate, triturating the residual concentrate with non-polar solvents, removing solvent by distillation under reduced pressure and below 45° C., obtaining the lipid soluble extract, fractionating the extract by column chromatography, obtaining fraction A, fraction B, and fraction C, and fractionating each of fractions A, B, and C further using HPLC or GLC to obtain the constituents.

In still another embodiment of the present invention, wherein fractioning the extract on silica gel column.

In still another embodiment of the present invention, wherein polar solvent is selected from a group comprising alcohol and acetone.

In still another embodiment of the present invention, wherein non-polar solvent is selected from a group comprising light petroleum and toluene.

In still another embodiment of the present invention, wherein wherein fractionating the extract using n-hexane, n-hexane: ethyl acetate mixture of ratio 95:5, and ethyl acetate successively.

In still another embodiment of the present invention, wherein fraction A constitutes about 75% of the said extract.

In still another embodiment of the present invention, wherein ar-turmerone constitutes 95% of the fraction A.

In still another embodiment of the present invention, wherein pressure is ranging between 7 and 11 mmHg.

In still another embodiment of the present invention, wherein concentration of the extract is about 6%.

In still another embodiment of the present invention, wherein a method of treating neurocerebrovascular disorders in animals including humans using composition of claim 1, by administering therapeutically effective amount of lipid soluble extract.

In still another embodiment of the present invention, wherein said method involves inhibiting nitric oxide synthase (NOS) overproduction, prevention calcium overload in neurons, and scavenging free radicals.

In still another embodiment of the present invention, wherein wherein cerebrovascular disorders are selected from a group comprising ischaemia, stroke, post-stroke injury, hemorrhage, reperfusion injury, thrombosis, vasoconstriction, nitric oxide-induced free radical oxidative damage, infraction, inflammation, and Alzheimer's disease.

In still another embodiment of the present invention, wherein fraction A of the composition is most effective.

In still another embodiment of the present invention, wherein said diseases are treated using the said composition is the form of various delivery systems selected from a group comprising tablets, capsules, suppository, beads, and aerosols.

In still another embodiment of the present invention, two novel compounds of formulae 3 and 4.

In still another embodiment of the present invention, a method of treating Ischaemia in animals including humans using composition of claim 1, said method comprises step of administering therapeutically effective amount to the subject.

In still another embodiment of the present invention, wherein said method helps treat severe brain ischaemia.

In still another embodiment of the present invention, wherein the effective amount is ranging between 10–1000 mg/day in divide dosage schedule.

In still another embodiment of the present invention, wherein the said composition is administered through various routes comprising i.p., and p.o.

In still another embodiment of the present invention, wherein said method prevents overload of calcium ions in the mitochondria.

In still another embodiment of the present invention, wherein the fraction A is most effective.

In still another embodiment of the present invention, a method of treating stroke in animals including humans using composition of claim 1, said method comprises step of administering therapeutically effective amount to the subject.

In still another embodiment of the present invention, wherein treating strokes selected from a group comprising thrombotic, embolic, and focal.

In still another embodiment of the present invention, wherein the effective amount is ranging between 10—In still another embodiment of the present invention, 1000 mg/day in divide dosage schedule.

In still another embodiment of the present invention, wherein the said composition is administered through various routes comprising i.p., and p.o.

In still another embodiment of the present invention, wherein the fraction A is most effective.

In still another embodiment of the present invention, a method of treating hemorrhage in animals including humans using a composition obtained from the lipid soluble extract of rhizomes and leaves of *Curcuma* species of Zingaberaceae, said method comprises step of administering therapeutically effective amount to the subject.

In still another embodiment of the present invention, wherein the effective amount is ranging between 10–500 mg/day in divide dosage schedule.

In still another embodiment of the present invention, wherein the said composition is administered through various routes comprising i.p., and p.o.

In still another embodiment of the present invention, wherein the fraction A is most effective.

In still another embodiment of the present invention, a method of treating throbosis in animals including humans using composition of claim 1, said method comprises step of administering therapeutically effective amount to the subject.

In still another embodiment of the present invention, wherein thrombosis is selected from a group comprising cerebral, coronary, and deep vein.

In still another embodiment of the present invention, wherein the effective amount is ranging between 10–1000 mg/day in divide dosage schedule.

In still another embodiment of the present invention, wherein the said composition is administered through various routes comprising i.p., and p.o.

In still another embodiment of the present invention, wherein the said method brings down the thrombus to one-fourth.

In still another embodiment of the present invention, wherein the fraction A is most effective.

In still another embodiment of the present invention, A method of treating hypertension in animals including humans using composition of claim 1, said method comprises step of administering therapeutically effective amount to the subject.

In still another embodiment of the present invention, wherein the effective amount is ranging between 10–1000 mg/day in divide dosage schedule.

In still another embodiment of the present invention, wherein the said composition is administered through various routes comprising i.p., and p.o.

In still another embodiment of the present invention, wherein the said method brings down the blood pressure by about 40%.

In still another embodiment of the present invention, wherein the said method maintains the blood pressure of normotensives.

In still another embodiment of the present invention, wherein the fraction A is most effective.

In still another embodiment of the present invention, a method of treating vasoconstriction in animals including humans using composition of claim 1, said method comprises step of administering therapeutically effective amount to the subject.

In still another embodiment of the present invention, wherein the effective amount is ranging between 10–1000 mg/day in divide dosage schedule.

In still another embodiment of the present invention, wherein the said composition is administered through various routes comprising i.p., and p.o.

In still another embodiment of the present invention, wherein the fraction A is most effective.

In still another embodiment of the present invention, and nitric oxide-induced free radical oxidative damage in animals including humans using composition of claim 1, said method comprises step of administering therapeutically effective amount to the subject.

In still another embodiment of the present invention, wherein said method augments the level of oxygen scavenging enzymes comprising superoxide dismutase (SOD), and catalase.

In still another embodiment of the present invention, wherein said method decreases the level of thiobarbituric acid reactive substances (TBARS).

In still another embodiment of the present invention, wherein the effective amount is ranging between 10–1000 mg/day in divide dosage schedule.

In still another embodiment of the present invention, wherein the said composition is administered through various routes comprising i.p., and p.o.

In still another embodiment of the present invention, wherein the fraction A is most effective.

In still another embodiment of the present invention, animals including humans using composition of claim 1, said method comprises step of administering therapeutically effective amount to the subject.

In still another embodiments of the present invention, said method involves treating various kinds of edema selected from a group comprising brain and pulmonary edema.

In still another embodiment of the present invention, wherein the effective amount is ranging between 10–1000 mg/day in divide dosage schedule.

In still another embodiment of the present invention, wherein the said composition is administered through various routes comprising i.p., and p.o.

In still another embodiment of the present invention, wherein the fraction A is most effective.

In an embodiment of the present invention powdering dry rhizomes and leaves into fine particles.

In another embodiment of the present invention percolating said powder with organic solvent at room temperature.

In yet another embodiment of the present invention stirring the contents continuously during percolation.

In still another embodiment of the present invention removing the said organic solvent by distillation under reduced pressure below 45° C.

In still another embodiment of the present invention repeating the above mentioned percolation steps at least 4–8 times.

In still another embodiment of the present invention collecting *Curcuma* oil as orange yellow odoriferous liquid at 5–8% yield, and In still another embodiment of the present invention separating said oil into its constituents by using techniques like Chromatography and distillation under high vacuum.

In still another embodiment of the present invention *Curcuma* species is selected from a group comprising *Curcuma longa* L.Syn. *Curcuma domestica* Valeton, and *Curcuma aromatica* Salisb.

In still another embodiment of the present invention the organic solvent is non-polar organic solvent selected from a group comprising light petroleum, and toluene.

In still another embodiment of the present invention the organic solvent is polar organic solvent selected from a group comprising ethanol, and propanol.

In still another embodiment of the present invention non-polar organic solvents give higher yield as compared to polar organic solvents.

In still another embodiment of the present invention the residual concentrate from polar organic solvent extract is extracted with non-polar organic solvent.

In still another embodiment of the present invention *Curcuma* oil is separated into its individual constituents comprising ar-d-turmerone (formula 1), turmerones of α and β (formula 2), zingiberine, curcumene, germacrone, curcumenone, and curlone.

In still another embodiment of the present invention kind of the Chromatography is selected from a group comprising Column Chromatography preferably High Performance Liquid Chromatography, and Gas-Liquid Chromatography.

In still another embodiment of the present invention the adsorbent for the Chromatography is selected from a group comprising alumina, and silica gel.

In still another embodiment of the present invention the elution of the said constituents is with organic solvent selected from a group comprising n-hexane, ethyl acetate, and n-hexane and ethyl acetate mixture in varying proportions.

In still another embodiment of the present invention molecular weight of the individual constituents of *Curcuma* oil separated by chromatography is turmerones (α-,β-)—mol. wt. 218, ar-d-turmerone—mol. wt. 216, zingiberine—mol. wt. 204, and Curcumene—mol. wt. 202.

In still another embodiment of the present invention retention time of the individual constituents of *Curcuma* oil separated by chromatography is turmerones (α-, β-)—retention time 9'-04", ar-d-turmerone—retention time 8'-08", zingiberine—retention time 5'-04", and Curcumene—retention time 4'-24".

Novel compound of the formula 3, an analog of compounds comprising ar-d-turmerone, turmerone, and germacrone wherein, R represents an alkyl, alkenyl, cycloalkane, phenyl, cycloalkene, or cycloalkadiene group, with substituents like alkyl, or alkoxy halo, in the phenyl, cycloalkene, cycloalkadiene rings, or hetroaryl like pyridyl nitrogen heterocyclic amine and substituted amines, and R1 represents alkyl or arylalkyl group.

Novel Compound of the formula 4, an analog of compounds comprising Procurcumenol, zedoarondiol, and curcumenone.

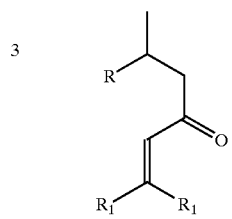

3

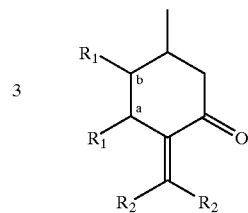

4

$CHR_1$—$CHR_1$=Phenyl, Substituted phenyl or=a b Δ, H,
$R_2$=H, or cd Δ,
$R_3$=Lower alkyl $C_{1-3}$ Pharmaceutical composition useful for treatment of Neurocerebrovascular disorders, said composition comprising effective amount of the lipid soluble extract called *Curcuma* oil, from rhizomes and leaves of species of plant Zingiberaceac family particularly *Curcuma* species, either as such or its individual constituents singly or in combination with each other or related compounds comprising melatonin, and tissue plasminogen activatior (t-PA), optionally associated with pharmaceutically acceptable additives.

In still another embodiment of the present invention is used to treat, reduce, control and prevent diseases conditions relating to increased production of nitric oxide (NO), injury due to inflammation, increased calcium entry and free radical oxidative damage to important biomolecules.

In still another embodiment of the present invention wherein, the additive is selected from a group of nutrients comprising proteins, carbohydrates, sugar, talc, magnesium stearate, cellulose, calcium carbonate, starch-gelatin paste, and/or pharmaceutically acceptable carrier, excipient, diluent, or solvent.

In still another embodiment of the present invention is administered orally, inhaled, or implanted.

In still another embodiment of the present invention wherein, physical state of the said composition for the oral route is in the form of capsule, tablet, syrup, concentrate, powder, granule, aerosol, or beads.

In still another embodiment of the present invention is administered at dosage level ranging between 5 to 5000 mg/day.

In still another embodiment of the present invention is used for treating animals or human beings.

In still another embodiment of the present invention is used for treating hypertension.

In still another embodiment of the present invention is used for treating cerebral and pulmonary edema which accompanies cerebral and myocardial infarction.

In still another embodiment of the present invention is used for treating reperfusion injury.

In still another embodiment of the present invention is used for treating cerebrovascular diseases comprising strokes, and transient ischaemic attacks.

In still another embodiment of the present invention is used for treating all kind of strokes comprising thromotic, embolic, focal and recurrent.

In still another embodiment of the present invention is used for treating subarachnoid and cerebral hemorrhage.

In still another embodiment of the present invention is used for treating neurological dysfunction.

In still another embodiment of the present invention is used for treating thrombosis infraction comprising cerebral, coronary, and deep vein.

In still another embodiment of the present invention is used for treating cancer.

In still another embodiment of the present invention is used for treating Alzheimer's disease wounds.

In still another embodiment of the present invention is used for treating Acquired Immunodeficiency Syndrome.

In still another embodiment of the present invention is used for treating migraine.

In still another embodiment of the present invention is administered again in case of relapse conditions.

A method of treating a subject for Neurocerebrovascular disorder conditions, said method comprising administering to the subject effective amount of the lipid soluble extract called Curcuma oil, from rhizomes and leaves of species of plant Zingiberaceae family particularly Curcuma species, either as such or its individual constituents singly or in combination with each other or related compounds comprising melatonin, and tissue plasminogen activatior (t-PA), optionally associated with pharmaceutically acceptable additives.

In still another embodiment of the present invention, is used for treating animals or human beings.

In still another embodiment of the present invention the additive is selected from a group of nutrients comprising proteins, carbohydrates, sugar, talc, magnesium stearate, cellulose, calcium carbonate, starch-gelatin paste, and/or pharmaceutically acceptable carrier, excipient, diluent or solvent.

In still another embodiment of the present invention the composition is administered orally, inhaled, or implanted.

In still another embodiment of the present invention the physical state of said composition for the oral route is in the form of capsule, tablet, syrup, concentrate, powder, granule, aerosol, or beads.

In still another embodiment of the present invention the composition is administered at a dosage level ranging between 5 to 5000 mg/day.

In still another embodiment of the present invention the composition is used for treating hypertension.

In still another embodiment of the present invention the composition is used for treating cerebral, and pulmonary edema which accompanies cerebral, and myocardial infarction.

In still another embodiment of the present invention the composition is used for treating post-stroke injury.

In still another embodiment of the present invention the composition is used for treating reperfusion injury.

In still another embodiment of the present invention the composition is used for treating cerebrovascular diseases comprising strokes, and transient ischaemic attacks.

In still another embodiment of the present invention the composition is used for treating all kind of strokes comprising thromotic, embolic, focal, and recurrent.

In still another embodiment of the present invention the composition is used for treating subarachnoid, and cerebral hemorrhage.

In still another embodiment of the present invention the composition is used for treating neurological dysfunction.

In still another embodiment of the present invention the composition is used for treating thrombosis infraction comprising cerebral, coronary, and deep vein.

In still another embodiment of the present invention the composition is used for treating cancer.

In still another embodiment of the present invention the composition is used for treating Alzheimer's disease wounds In still another embodiment of the present invention the composition is used for treating Acquired Immunodeficiency Syndrome.

In still another embodiment of the present invention the composition is used for treating migraine.

In still another embodiment of the present invention the composition is administered again in case of relapse conditions.

In an embodiment of the present invention, obtain/prepare therapeutically effective medicaments from extracts of Curcuma species rhizomes and leaves which belong to Zingiberaceae family.

In another embodiment of the present invention, more particularly, the lipid soluble extract/fraction of Curcuma longa L. syn. Curcuma domestica Valeton, commonly known as turmeric or Haldi.

In another embodiment of the present invention, in pharmaceutically acceptable formulations/delivery systems such as tablets, capsules, suppository, beads, aerosols, etc. for the treatment and prevention of human diseases in which increased production of Nitric Oxide (NO) and free radical oxidative damage are implicated.

In another embodiment of the present invention, such diseases are neurocerebrovascular disorders like transient ischaemic attacks (ischaemic, hemorrhagic, focal recurrent etc.) thrombosis (cerebral, coronary, deep vein), infarction, stroke (thrombotic, embolic, focal etc.), Alzheimer's disease, inflammatory, neurological dysfunctions, wounds, carcinogenesis, tumor progression etc.

In another embodiment of the present invention, the superoxide and nitric oxide (NO) scavenging property of the lipid soluble extract/fraction of Curcuma species rhizomes (Family: Zingieraceae) especially Curcuma longa L. Syn. Curcuma domestica Valeton, hereinafter referred to as Curcuma oil either as such or its various constituents singly or in combination with each other which makes them therapeutically effective to control various degenerative diseases, more particularly a drug which is nitric Oxide (NO) and superoxide scavenger with anti-inflammatory activity to combat brain and pulmonary edema/swelling which accompanies brain and myocardial infarction.

In another embodiment of the present invention, Keeping these biological profiles in view and as a follow-up of the holistic view of Ayurveda of human diseases, the lipid soluble extract/material of Curcuma species rhizomes and leaves (Zingiberaceae family) hereinafter referred to as Curcuma oil and obtained from Curcuma longa L.syn. Curcuma domestica Valeton, rhizomes and leaves, either as such or its major active constituents, ar-d-turmerone (formula 1), turmerones ($\alpha$-,$\beta$-,formula 2) either singly or in combination with each other with and with the other minor constituents are found to be significantly beneficial and possess powerful Nitric oxide(NO) and free radical/superoxide scavenging activity.

In another embodiment of the present invention, said lipid soluble extract exhibit/possess potent free radical scavenging/antioxidant activity which enables them to protect mitochondrial impairment protecting downstream target and they inhibit overproduction of nitric oxide synthase (NOS), avoid injury due to inflammation and reduce calcium entry so that the resultant calcium overload in the neurons does not occur.

In another embodiment of the present invention, another important advantage is that if there is any blockage, the above three parameters which are the major cause of reperfusion injury are taken care of by these medicaments and the collaterals from the "Circle of Willis" are able to help in the blood flow and thereby enable the drug to reach the site of injury.

In another embodiment of the present invention, cases where severe brain ischaemia has occurred, administration of Curcuma oil either as such or its individual constituents such as ar-d-turmerone, turmerones etc. singly or in combination with each other with and without other related compounds of the type of formula 3 or 4 and/or other therapeutically beneficial agents such as melatonin, other antioxidants, calcium channel antagonists, tissue plasminogen activator (t-PA) and cell membrane stabilizing agents can provide effective protection against cerebral and even coronary damage.

In another embodiment of the present invention, since stroke is one of the main causes of the mortality among hypertensive patients, our finding also underline the importance of the *Curcuma* oil either as such or its individual constituents either alone or in combination with each other as an effective anti-hypertensive drug with antioxidant and neuro protective activities.

In another embodiment of the present invention, the lipid soluble extract of rhizomes and leaves of *Curcuma* species of the family zingiberaceae especially *Curcuma longa* L.syn. *Curcuma domestica* Valeton hereinbefore referred to as Curcuma oil which is a pale yellow to orange yellow odoriferous oily liquid whose major constituents are: ar-d-turmerone(formula 1), turmerones (α-, β-, formula 2)[Tap Chi Hoa Hoc: 25,18(1987); Chem. Abstr., 108, 137682$^s$ (1988)] besides other minor constituents such as zingiberine, curcumene, curlone, curculone, curzenone, α-,β-curcumenolides, curcumenone, curdione, germacrone, linalool, camphor, borneol, zingiberol etc. [Essenze Deriv. Agrum, 54, 117(1984); Chem Abstr., 103, 128791$^w$ (1985)] inhibits increased production of nitric oxide (NO) and is a free radical scavenger/antioxidant which can penetrate the blood brain barrier and provide effective therapeutic protection by combating nitric oxide(NO)and superoxide/free radical induced neuronal injury/damage in human diseases such as neurocerebrovascular dysfunctions, all types of strokes, thrombosis (cerebral, coronary, deep vein), infarction, inflammatory and neurological disorders, certain types of cancer, wounds, Alzheimers disease and other nitric oxide neurotoxicity, hyperbaric oxygen exposure etc.

In another embodiment of the present invention, high yields of the lipid soluble material is obtained from *Curcuma* species rhizomes and leaves (Family: Zingiberaceae), particularly *Curcuma longa* L. syn. *Curcuma domestica* Valeton, hereinafter referred to as *Curcuma* oil and isolation of its various constituents.

In another embodiment of the present invention, more particularly this invention relates to nitric oxide (NO) and superoxide scavenging activity and prevention of any changes in cerebral blood flow dynamics by *Curcuma* oil itself or by its constituents singly or in combination with one another which enables their use as medicaments for the treatment and prevention of neurocerebrovascular disorders and related and unrelated dysfunctions such as ischemic attacks, all types of stroke, thrombosis, infarction, migraine, Alzheimer's disease, inflammatory and neurological dysfunctions, carcinogensis, tumor progression wounds and even HIV/AIDS.

Novel compound of the formula 3, an analog of compounds comprising ar-d-turmerone, turmerone, and germacrone wherein, R represents an alkyl, alkenyl, cycloalkane, phenyl, cycloalkene, or cycloalkadiene group, with substituents like alkyl, or alkoxy halo, in the phenyl, cycloalkene, cycloalkadiene rings, or hetroaryl like pyridyl nitrogen heterocyclic amine and substituted amines, and R1 represents alkyl or arylalkyl group.

Novel Compound of the formula 4, an analog of compounds comprising Procurcumenol, zedoarondiol, and curcumenone.

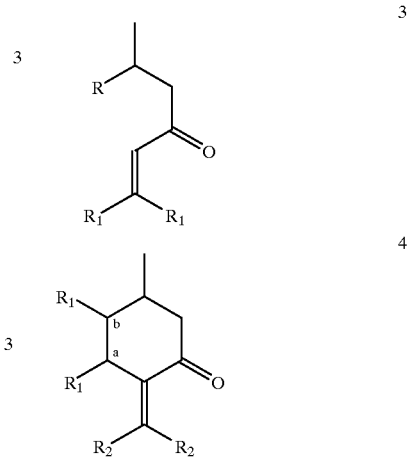

$CHR_1$—$CHR_1$=Phenyl, Substituted phenyl or=a b Δ, H,
$R_2$=H, or cd Δ,
$R_3$=Lower alkyl $C_{1-3}$

BRIEF DESCRIPTION OF THE ACCOMPANY DRAWINGS

Figure 1:
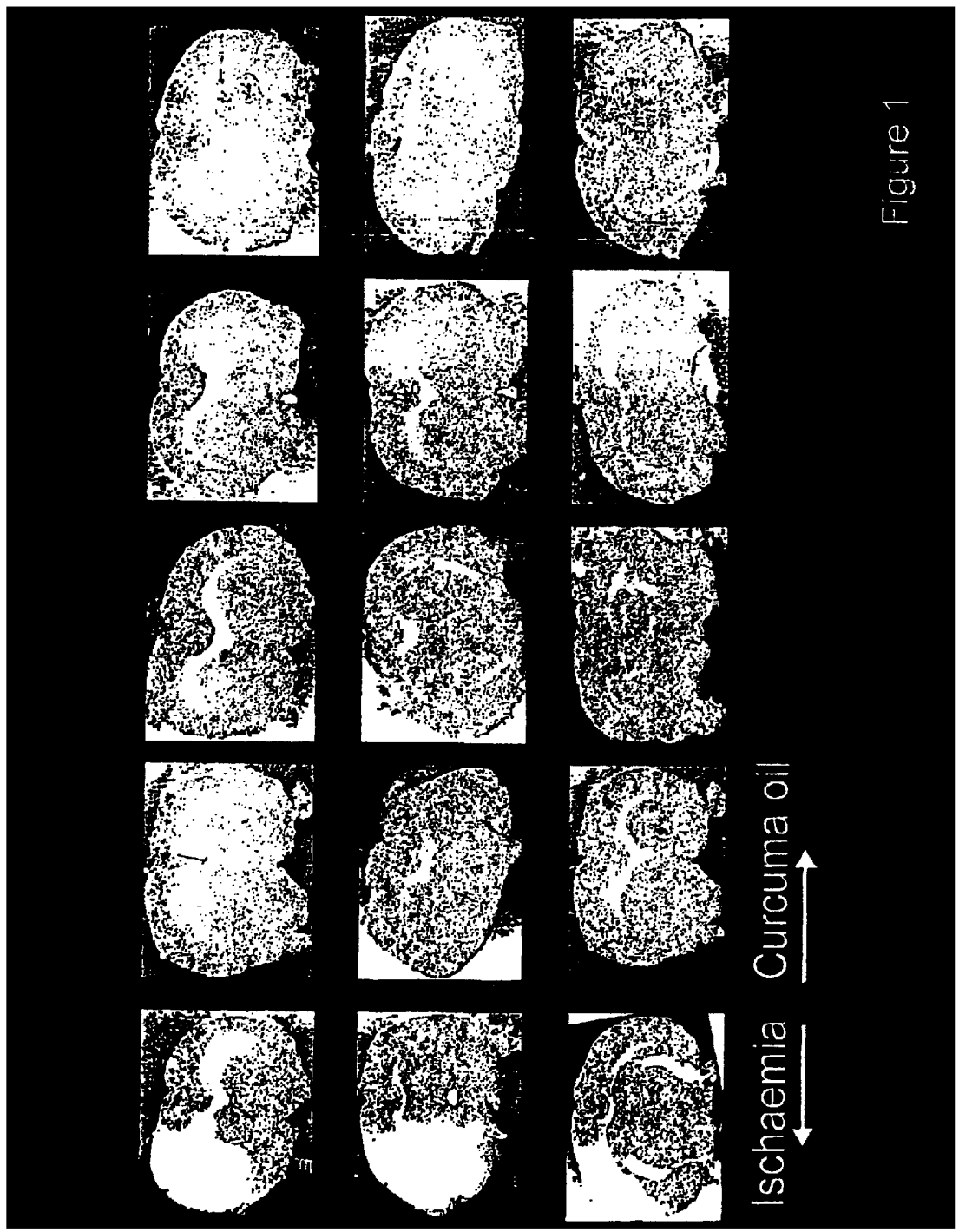
FIG. 1 shows prevention of infarction from focal ischaemic rat after using curcuma oil.

In another embodiment of the present invention, provides a method of obtaining the lipid soluble extract/fraction of rhizomes and leaves of various species belonging to zingiberaceae family, especially *Curcuma* oil from *Curcuma* species in good yield by extraction of powdered rhizomes/leaves of *Curcuma longa* L. Syn. *Curcuma domestica* Valeton or *Curcuma aromatica* Salisb or *Curcuma zedoaria* Roxb. etc. with an organic solvent like alcohol, acetone, ethyl acetate etc. but preferably a non-polar organic solvent like light-petroleum or toluene under constant stirring and removing the solvent from such extracts by distillation under reduced pressure below 45° C.

In another embodiment of the present invention, in the case of extraction by a polar organic solvent such as ethanol, the residual alcoholic concentrate after removal of the solvent is exhaustively extracted with a non-polar organic solvent like light-petroleum, toluene etc.

In another embodiment of the present invention, distillation of solvent from such extracts under reduced pressure below 45° C. yields a pale yellow to orange yellow odoriferous liquid in 5 to 6 per cent yields.

In another embodiment of the present invention, fractionation of this oil by column chromatography over a suitable adsorbent and elution by an appropriate organic solvent or by HPLC or GLC or distillation in vacuum yields the individual constituents such as ar-d-turmerone (formula 1), turmerones (α-,β-, formula 2) as major constituents (about 70 percent as determined by GC-MS) besides other minor constituents like zingiberine, curcumene, zedeorone, germacrone, curlone, curdione etc. all identified by GC-MS etc.

In another embodiment of the present invention, an improved method of obtaining the lipid soluble extract/material of rhizomes and leaves of various species of Zingiberaceae family especially *Curcuma* species such as *Curcuma longa* L.Syn. *Curcuma domestica* Valeton or *Curcuma aromatica* Salisb. etc. in high yields by exhaustive extraction of finely powdered rhizomes or leaves with an appropriate organic solvent under continous gradual stirring or by sonication at ordinary room temperature followed by removal of the solvent from the extract by distillation under reduced pressure below 45° C.

In another embodiment of the present invention, the organic solvent is a non-polar organic solvent such as light petroleum, toluene etc.

In another embodiment of the present invention, the organic solvent used is a polar organic solvent such as ethanol, propanol etc.

In another embodiment of the present invention, the residual concentrate after removal of the solvent from the polar organic solvent extract is exhaustively extracted with a non-polar organic solvent such as light-petroleum, toluene etc.

In another embodiment of the present invention, the organic solvent is removed from the extracts by distillation under reduced pressure below 45° C.

In another embodiment of the present invention, the continues' stirring is done either manually or by a mechanical stirrer or by an electric motor.

In another embodiment of the present invention, the lipid soluble extract/material of rhizomes or leaves of said species, which, is a pale yellow to orange-yellow odoriferous oily liquid, is separated into its individual constituents such as ar-d-turmerone (formula 1), turmerones (α,β- formula 2), zingiberine, curcumene, germacrone, curcumenone, curlone etc. by chromatography (column, HPLC, GLC etc.) or distillation under high vacuum.

In another embodiment of the present invention, the individual constituents of the *Curcuma* oil are obtained by column chromatography over a suitable adsorbent such as alumina, silica gel etc. and elution by appropriate organic solvents such as n-hexane, n-hexane: ethyl acetate mixture (in varying proportions), ethyl acetate etc.

In another embodiment of the present invention, the individual constituents of *Curcuma* oil are obtained by HPLC or GLC, e.g. turmerones (α-,β-), mol. wt. 218, retention time 9'-04", ar-d-turmerone (mol. wt. 216), retention time 8'-08", zingiberine (mol. wt. 204) retention time 5'-04", Curcumene (mol. wt. 202), retention time 4'-24".

In another embodiment of the present invention, the individual constituents of *Curcuma* oil, such as ar-d-turmerone (formula 1), turmerones (formula 2), zinziberine, curcumene, curcumenone, germacrone etc. are obtained by distillation of *Curcuma* oil in vacuum, e.g. ar-d-turmerone, b.p. 155–160° C./9 mm Hg through ar-d-turmerone rich fraction, b.p. 140–160° C./10 mm Hg which is about 70% of the whole *Curcuma* oil In another embodiment of the present invention, Nitric oxide (NO) and superoxide scavenging (anti-oxidant) property of the said lipid soluble extracts individual constituents such as ar-d-turmerone (FIG. 1), termerones (FIG. 2), germacrone, curcumenone, zingiberine, curcu-meneetc either as such or it individual constituents.

In another embodiment of the present invention, compounds of the formula 3 as analogs of ar-d-turmerone or turmerone, germacrone etc. when R represents an alkyl, alkenyl, cycloalkane, phenyl, cycloalk-ene or cycloalkadiene with substituents like alkyl, alkoxy halo-etc. in the phenyl or cycloalkene or cycloalkadiene rings, hetroaryl like pyridyl nitrogen heterocyclic, amine or substituted amine etc. and R1=alkyl, arylalkyl etc. as nitric oxide (NO), superoxide/free radicals scavengers to combat/prevent nitric oxide (NO), superoxide/free radical oxidative damage to important bio molecules.

In another embodiment of the present invention, compounds of the type-

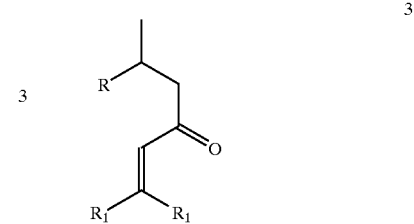

3 formula 4 as analogs of Procurcumenol, zedoarondiol, curcum-enone etc.-the other minor constituents of the lipid soluble extract of the *Curcuma* species which incorporate in their molecular architecture the salient features of ar-d-turmerone and turmerone (α-,β-) molecules in a rigid frame work as therapeutically beneficial medicaments for the treatment and prevention of all types of stroke, thrombosis, infarction, neurological dysfunctions etc.

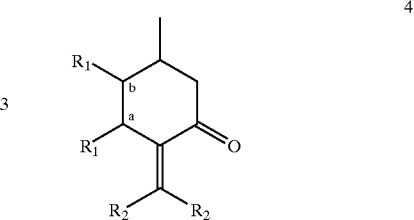

4

$CHR_1$—$CHR_1$=Phenyl, Substituted phenyl or=a b Δ, H
$R_2$=H, or cd Δ,
$R_3$=Lower alkyl $C_{1-3}$ In another embodiment of the present invention, therapeutically beneficial effects of *Curcuma* oil as such or its individual constituents singly or in combination with each other or of related compounds, reduce, control or prevent human diseases in which increased production of nitric oxide (NO) and free radical oxidative damage to important biomolecules is implicated such as all types of stroke (thrombotic, embolic, focal, ischaemic), thrombosis (cerebral, coronary, deep vein) infarction, neurological dysfunctions etc.

In another embodiment of the present invention, method of treating post-stroke injury in mammals which comprises administering to a subject in need thereof an effective amount of *Curcuma* oil either as such or its individual constituents singly or in combination with each other or related compounds.

In another embodiment of the present invention, method of treating patients of Subarachnoid and cerebral hemorrhagic stroke after 5 to 7 hours of the stroke by administering to a subject in need thereof a therapeutically effective amount of *Curcuma* oil either as such (whole) or its individual constituents singly or in combination with each other or related compounds.

In another embodiment of the present invention, method of treating reperfusion injury in mammals that comprises administering to a subject in need thereof an effective amount of *Curcuma* oil (whole-as such) or its individual constituents singly or in combination with each other or related compounds.

In another embodiment of the present invention, method of treating cerebrovascular diseases like all types of stroke (thrombotic, embolic, focal, recurrent), transient ischaemic attacks etc. by administering to a subject in need thereof an effective amount of *Curcuma* oil (whole-as such) or its individual constituents singly or in combination with each other or related compounds.

In another embodiment of the present invention, method of treating ischaemic diseases and prevent dangerous blood clot formation by administering to a subject in need thereof an effective amount of *Curcuma* oil (whole) or its individual constituents singly or in combination with each other or related compounds.

In another embodiment of the present invention, method for treating hypertension in mammals that comprises administering to a subject/patient in need thereof an effective amount of *Curcuma* oil (whole) or its individual constituents singly or in combination with each other or related compounds.

In another embodiment of the present invention, method to combat cerebral and pulmonary edema which accompanies cerebral and myocardial infarction by administering to a subject in need thereof medicaments like *Curcuma* oil (whole) or its individual constituents singly or in combination with each other or related compounds, which are nitric oxide (NO) and superoxide/free radicals scavengers with anti-inflammatory activity.

In another embodiment of the present invention, therapeutically beneficial effects of the SAID lipid soluble extracts, either as such or its individual constituents like ar-d-turmerone, turmerones, germacrone, zinziberine, curcumene, curlone etc. singly or in combination with each other with and without other therapeutically useful agents such as melatonin, tissue plasminogen activator (t-PA) administered orally, parentally (individual pure constituents) or in any other appropriate pharmaceutically acceptable delivery system such as tablets, capsules, beads, suppositories aerosols, implants etc in an effective amount (for Stroke, 10–500 mg/daily in divided doses and for other Ailments, 0–10000 mg/daily in divided doses),to provide a highly effective cure/treatment for human diseases wherein nitric oxide (NO) and free radical oxidative damage are implicated such as all type of stroke, thrombosis, infarction and neurological dysfunctions and which may also be of therapeutic use in certain type of cancer such as leukemia, Alzheimer's disease wounds and even HIV./AIDS.

EXAMPLES

The following examples broadly illustrate the invention without in anyway limiting the nature and scope of the invention:

Example 1

This example describes the method of obtaining *Curcuma* oil and its constituents in high yields and preparation of its dosage formulations. Improved extraction procedure of *Curcuma* oil and its constituents from *Curcuma longs* L. syn. *Curcuma domestica* Valeton or other *Curcuma* species rhizomes.

The usual extractive procedure employs three or four percolations of dry powdered *Curcuma* rhizomes with an organic solvent like light petroleum, toluene, alcohol etc. and distillation of the solvent from the percolates. In case of alcoholic extracts, after solvent removal the residual concentrate is triturated with a non-polar organic solvent like light petroleum followed by removal of the solvent by distillation to yield *Curcuma* oil in 1 to 1.5 percent yields.

Hot extraction (Soxhlet) leads to loss of essential volatile constituents. When these procedures were changed to extraction of the dry powdered *Curcuma* rhizomes with appropriate organic solvents such as light petroleum, acetone, alcohol etc. with continous stirring by mechanical stirrers driven by electric motors or manually or agitation with sonicator followed by removal of the solvent from the extracts by distillation under reduced pressure below 45° C. the yield and quality of the *Curcuma* oil increased appreciably.

In a typical procedure, dry finely powdered *Curcuma longa* L. rhizomes (1 kg) were successively percolated with n-hexane (3 liters) in a stainless steel or glass percolator/vessel fitted with a tap near the bottom to drain out the percolate, and the contents were stirred under slow motion continuously for 24 hours each time by a mechanical stirrer driven by an electric motor. The orange-yellow percolate was drained out and the procedure repeated four to five times. Solvent was distilled off from the percolates under reduced pressure below 45° C. to yield an orange yellow odoriferous liquid (51 gms=5.1% yield).

Likewise, initial extraction of finely powdered *Curcuma longa* L rhizomes (1 kg) with acetone or alcohol (5×3 liters) under continuous stirring for 24 hours each time followed by removal of the solvent from the percolates by distillation under reduced pressure below 45° C. and exhaustive trituration of the residual concentrate with n-hexane or toluene (6×500 ml) followed by removal of the solvent by distillation under reduced pressure below 45° C. yielded an orange yellow odoriferous liquid (60 gm.=6% yield).

Column chromatography of this orange yellow odoriferous liquid (20.0 gm.) over a silica gel column, using n-hexane, n-hexane: ethyl acetate (in varying proportions) mixture and ethyl acetate successively gave ar-d-turmerone (formula 1, 55%) and turmerones (α-,β-formula 2, 20%) as major constituents (fraction-A.) followed by curcumene (10%) & zingiberine (fraction-B) and other minor constituents-germacrone, curcumerone, zedoarone, zedoarondiol, isozdedoarondiol, curcumenone, curlone etc. (fraction C) whose activity was low.

Distillation of *Curcuma* oil (20.0 gms.) under reduced pressure (140–160° C./9 mm Hg) yielded ar-d-turmerone rich major fraction I (formula 1, 15.0 gms)

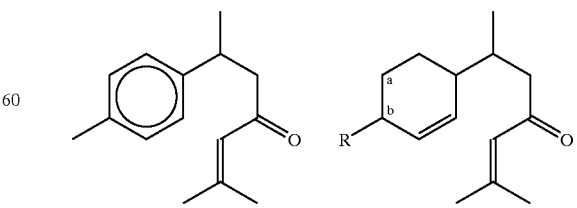

along with other turmerones (formula 2) and other minor constituents (4.2 gms, fraction II) Fraction I

| 1 | 2 |
|---|---|
| Ar-d-turmerone | α-turmerone, ab Δ and R = Me<br>β-Turmerone, R = =CH$_2$ | had refractive index ($n_D^{30}$) 1.4990, specific optical rotation $(L)^{25}$+19.6. *Curcuma* oil itself or its individual constituents obtained by chromatography or distillation under high vacuum are used singly or in combination with each other with and without other therapeutically beneficial compounds to prepare appropriate clinically effective formulations.

The solid dosage form may be obtained by maceration of *Curcuma* oil as such or its individual constituents singly or in combination with each other particularly ar-d-turmerone, α-,β-turmerones with starch and microcrystalline cellulose in suitable proportions in a mixer till the mixture becomes a free flowable powder which may be filled in capsules or converted into tablets as per therapeutically desired specifications. In a typical example, *Curcuma* oil (10.0 gm.) was dissolved in ethanol (100 ml). Starch (5.0 gm) and microcrystalline cellulose (85.0 gm) were added to this solution. The contents were mixed thoroughly and solvent was removed by drying below 45° C. The resulting product was passed through 40-mesh size sieve to obtain free flowing granules. These granules were then compressed into tablets of appropriate dosage requirements, e.g. each tablet weighing 500 mg.contain 50 mg of *Curcuma* oil.

Example 2

Focal Cerebral Ischaemia

Male Sprague Dawley rats of 270–375 gm weight from CDRI Animal House were used for this study. Rats were housed in a 12-hr. light/dark cycle and water was given ad libitum. Animals were fasted overnight and anaesthetized with pentobarbitone sodium, 30 mg/kg. Rectal temperature was monitored. Transient ischaemia/reperfusion was performed using an intravascular filament to occlude the middle cerebral artery unilaterally [Longa Z. E., Weinstein P. R., Carlson S., Cummins R.; Reversible middle cerebral artery occlusion without craniectomy in rats: Stroke, 20, 84–91 (1989)] for 2 hours followed by reperfusion for the remainder of 36 hours. Animals were assigned randomly to the following groups of n=5 rats (1) Control: Sham operated. (2.) Ischaemic/reflow- no treatment. (3.) Ischaemic/reflow-treated group:(i) *Curcuma* oil (weight/ml., 0.86 gm.), 683.65 mg./kg., given i.p. and P.O. (ii). Fraction-A(weight/ml., 0.88 gm.), 569.56 mg/kg., given, i.p. and P.O. (iii). Fraction-B. (weight/ml., 0.91 gm.) 938.86 mg/kg., given, i.p. and P.O. The animals were sacrificed & brains were removed and quickly frozen. Eight coronal section of of 2 mm thickness from each brain were cut and stained with 2,3,5-triphenyltetrazolium chloride at 37° C. for 30 min. and post fixed by formalin. Each brain slice was photographed. The area of infarct in each slice was evaluated in a double blind manner. From groups (1,2, & 3) rats n=3, brain was removed and processed for mitochondrial $Ca^{2+}$ estimation.

Experimental Protocol

Isolation of Forebrain Mitochondria

Mitochondria were isolated from the rat forebrain according to the method of Lai and Clark [Lai J. C. K., Clark J. P., Preparation of synaptic and non-synaptic mitochondria from mammalian brain: Method Enzymol., 55, 51–60(1979)] with slight modifications. Rat forebrain was immediately removed after decapitation and immersed in ice-cold isolation medium or Phosphate Buffered Saline. Brains were minced and rinsed to remove all the traces of blood. The tissue was homogenized (10% w/v) in an appropriate medium using a motorized Teflon homogenizer and immediately centrifuged at 1800 g for 10 min. The supernatant was decanted and the pellet rehomogenized and centrifuged at 1800 g for 10 min. Supernatants from the first and the second spins were added together and centrifuged at 17,000 g for 20 minutes. The resultant pellet was resuspended in specific mediums and centrifuged at 17000 g. for 5 minutes.

Determination of Mitochondrial Content

Calcium content of mitochondria isolated from forebrain was estimated according to the method of Zaidan E. and Sims N. R. [The calcium content of mitochondria from brain sub regions following short term fore brain ischaemia and recirculation in the rat; J. Neurochem., 63,1812–1819 (1994)] with slight modifications. In brief, mitochondria (0.3 mg. protein) in succinate mediun were loaded with Fura-2AM (0–5 μM) and incubated for 30 min. at 37° C. with constant shaking. The mitochondria were then washed twice in succinate medium and re-suspended in the same medium.

The ratio of Fura-2 fluorescence at exciting wavelength of 340 and 380 nm with emission at 510 nm was determined using a Shimadzu RF 5000 Spectrofluorometer. Mitochondrial Calcium($[Ca^{2+}]_m$), is presented as tracings of the 340/380 fluorescence ratio [Macleod K. T and Harding S. E.; Effect of phorbolester in contraction, intracellular pH and intracellular $Ca^{2+}$ in isolated mammalian ventricular myocytes. J. Physiol. (London), 444, 481–498 (1991)].

Result

Figure 2:
FIG. 2 shows past occlusion complete prevention of infarction in forebrain after using fraction A.
Figure 2:
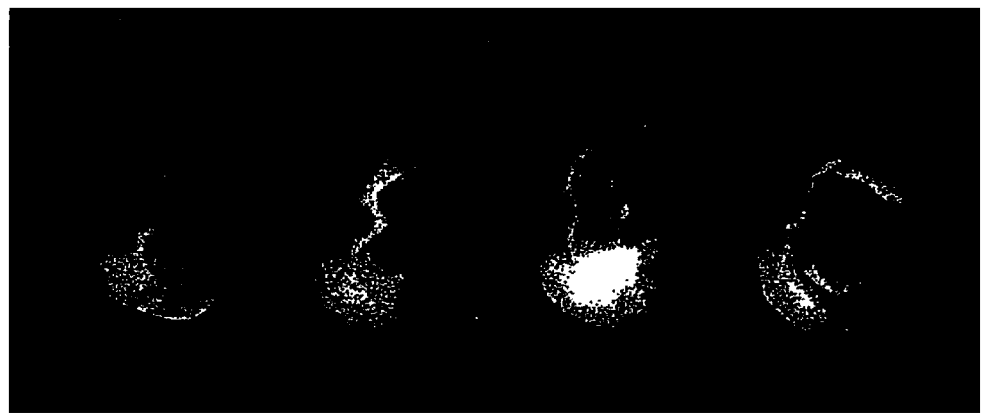
Figure 3:
FIG. 3 shows past occlusion complete prevention of infarction in forebrain after using fraction B.
Figure 3:
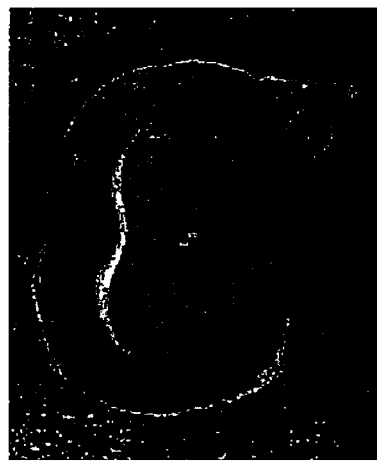
Figure 4:
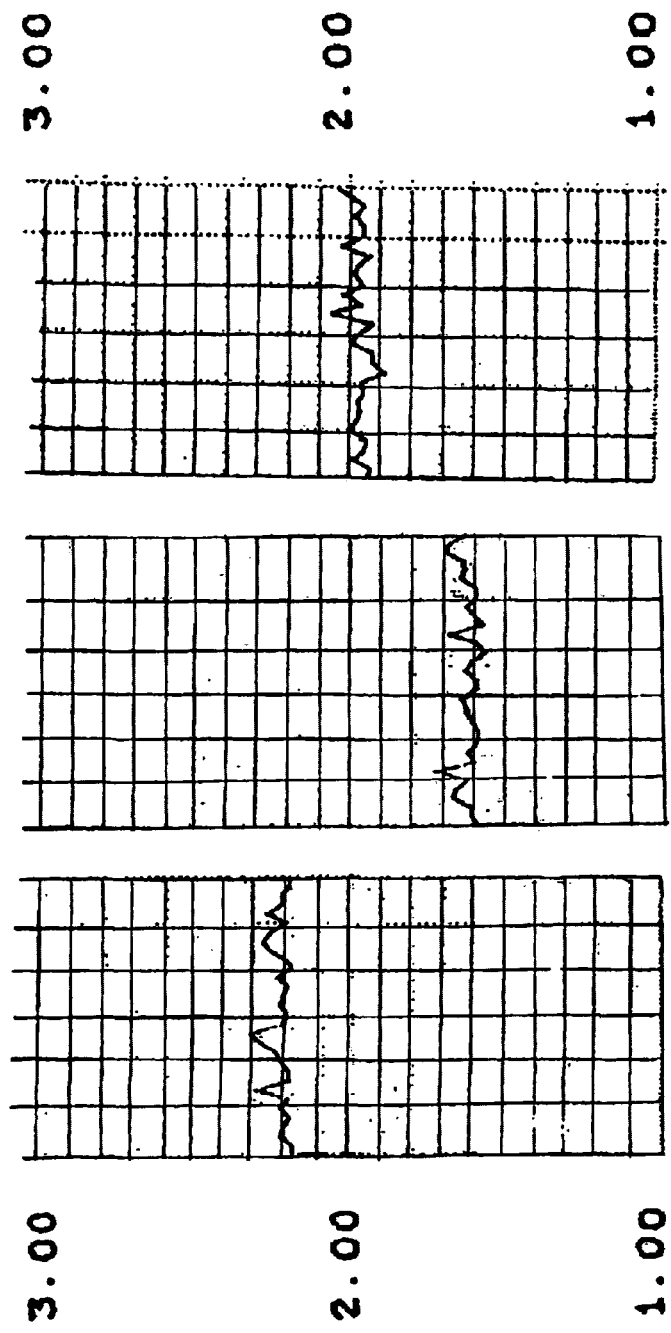
FIG. 4 shows Calcium transients in mitochondria (340/380 ratio)

Infarct from focal ischaemic rat in pretreated group was completely prevented as seen in FIGS. 1 & 2. In the group where test compound/agent was given post occlusion of middle cerebral artery, six out of seven brain sections shows complete prevention (FIG. 3), whereas in one about 20% of the area showed up as infarcted. Mitochondria isolated from forebrain from animals made sham, ischaemc and treated with the test compound group (i) showed the intracellular calcium levels close to normal (FIG. 4).

Example 3

Collagenase-Induced Intra-Cerebral Hemorrhage

Adult male rats (250–350 gm.) from the CDRI-Animal House were used in the following experiments. The rats were anaesthetized with pentobarbitone sodium (30 mg/kg, i.p.) and placed in a stereotaxic frame (for rats, Narashige, Japan). Rosenberg et. al's method [Rosenberg G. A. Mun-Bryce S., Mary B. S. and Komfeld M., Collagenase-Induced intracerebral hemorrhage in rats: Stroke, 21, 801–807 (1990)] was followed. An incision was made in the scalp and a 23-guage needle was implanted into the caudate nucleus and the putamen (at the coordinates of A5.8, L3.0, H1). (A stereotaxic atlas of the rat brain, eds. R. M. Elliot, Gardener Lindzey and Kenneth, MacCorquodale. Meredith Publishing Company, 1967). Rats(n=10) were injected with collagenase (0.01 IU in 2 μl of saline) and for sham with 2 μl of normal saline. After infusion, the needle was removed and the wound was sutured. The animals were allowed to recover from anesthesia, kept in a warm place and allowed access to food and water. Eighteen hours later, the animals were evaluated for neurological deficit by measuring scoring of abnormal possture and hemiplegia according to Yamamoto et. al. [Yamamoto A. Tamura, Kirino T., Shimizu M and Sano K. Behavioral changes after focal cerebral ischaemia by left middle cerebral artery occlusion in rats. Brain Research, 452, 323–328. (1988)]. Later rats were reanaesthetized with pentobarbitone sodium, 30-mg/kg i.p. and brain was removed. Rats were assigned randomly into three groups. Group 1, received saline. Collagenase (0.01 IU in 2 µl saline) treated Groups 2 & 3 received fraction A (683.65 mg/kg) after 5 and 7 hours of collagenase treatment by the oral route.

Antioxidant Estimations

Mitochondria were isolated as described in example 2. For antioxidant estimations, the mitochondria were rinsed and suspended in phosphate buffer. For the other estimations mitochondria were resuspended in a medium containing sucrose 250 mM, $KH_2PO_4$ 6 mM and succinate 6 mM, pH 7.2. The isolation procedure was carried out at 4° C.

Antioxidants

The oxygen scavenging enzymes, superoxide dismutase (SOD), catalase (CAT) and thiobarbituric acid reactive substances were estimated in mitochondria isolated from forebrain of experimental animals.

SOD: SOD activity was measured by the inhibition of NADH, PMS, NBT and absorbance monitored at 560 nm. Enzyme activity is expressed in U/min/mg protein. [Nishikini M., Rao N. A., Yagi K., The occurrence of superoxide anion in the reaction of reduced PMS and molecular oxygen. Biochem Biophysi. Res. Commun., 46, 849–854 (1972)].

CAT: CAT activity was assayed by measuring the UV absorbance change of $H_2O_2$ at 240 nm according to Aebi [Aebi H., In Methods of Enzymatic Analysis (Third edition) ed. H. U. Bergmeyer Academic Press, New York and London, Vol. 2 pp 673–684. (1974)]

Thiobarbituric acid reactive substance (TBARS):

Mitochondrial TBARS levels were measured as an index of malondialdehyde and hence lipid peroxidation by the method of Okhawa et. el. [Okhawa H., Ohishi N., Yagi K., Assay of lipid peroxides in animal tissues by thiobarbituric acid reaction: Anal. Biochem., 95, 351 (1979)] at 532 nm. Functional deficit was estimated according to Bederson [Bederson J. B., Pitts, L. H. Tsiji M., Nishimura M. C. Davis R. L., Barkowisk H., Rat MCAO: Evaluation of model and development of a neurologic examination, Stroke, 17, 472 (1986)] and water contents were estimated. Both the parameters were found to be significantly reduced as compared to untreated group.

Protein Assay

Mitochondrial protein was determined by the method of Lowry et.al. [Lowry O. H., Rosbrough N. J., Farr. A. L., Randall K. J.; Protein measurement with folin phenol reagent: J. Biol. Chem., 193, 265 (1951)] using bovine serum albumin(BSA) as standard.

Result

The test compound (fraction A) given 5 hours after collagenase treatment significantly reduced the edema. Neurological deficit at 5 & 7 hours of treatment were scored as grade 4 in untreated group and grade 0–2 in treated group. Mortality in untreated group was 3 out of 5 and in treated group 1 out of 5.

Figure 5:
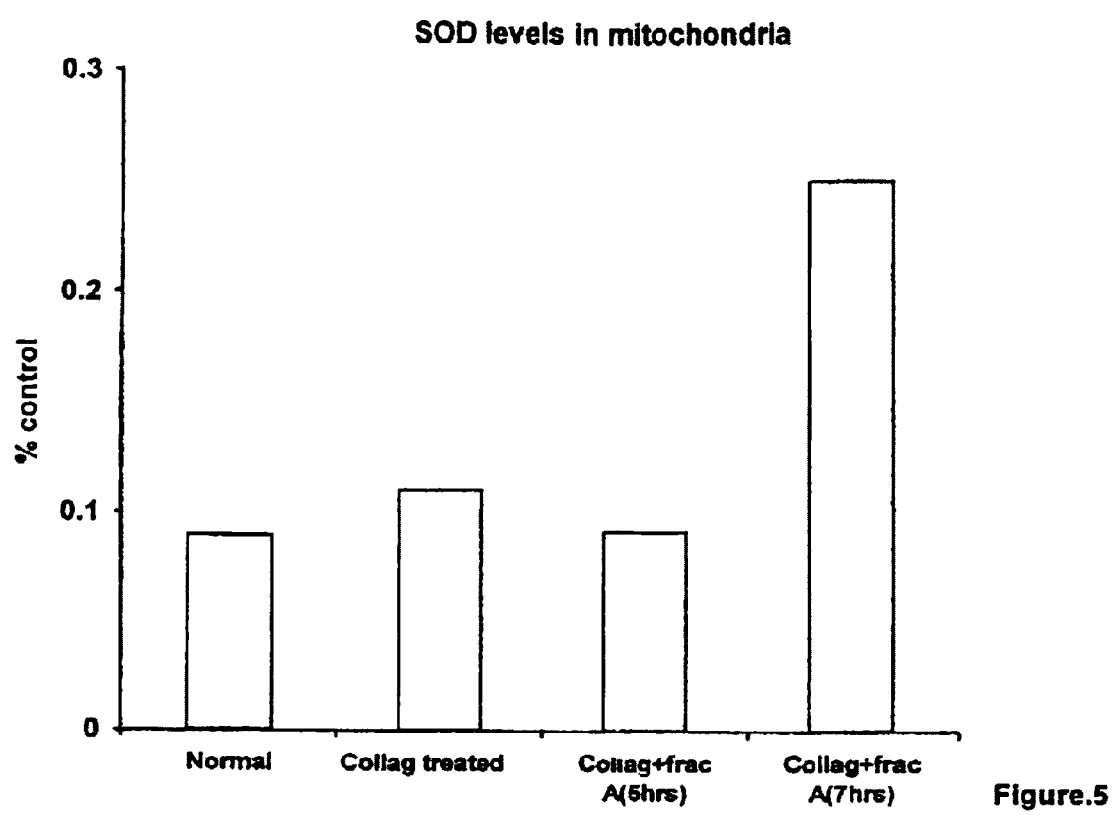
FIG. 5 shows change in SOD levels in mitochondria after using fraction A and fraction B.

SOD: SOD value in 5 hours was almost normal while in case of test compound (fraction A) given after 7 hours post collagenase treatment the SOD levels were augmented (FIG. 5).

Figure 6:
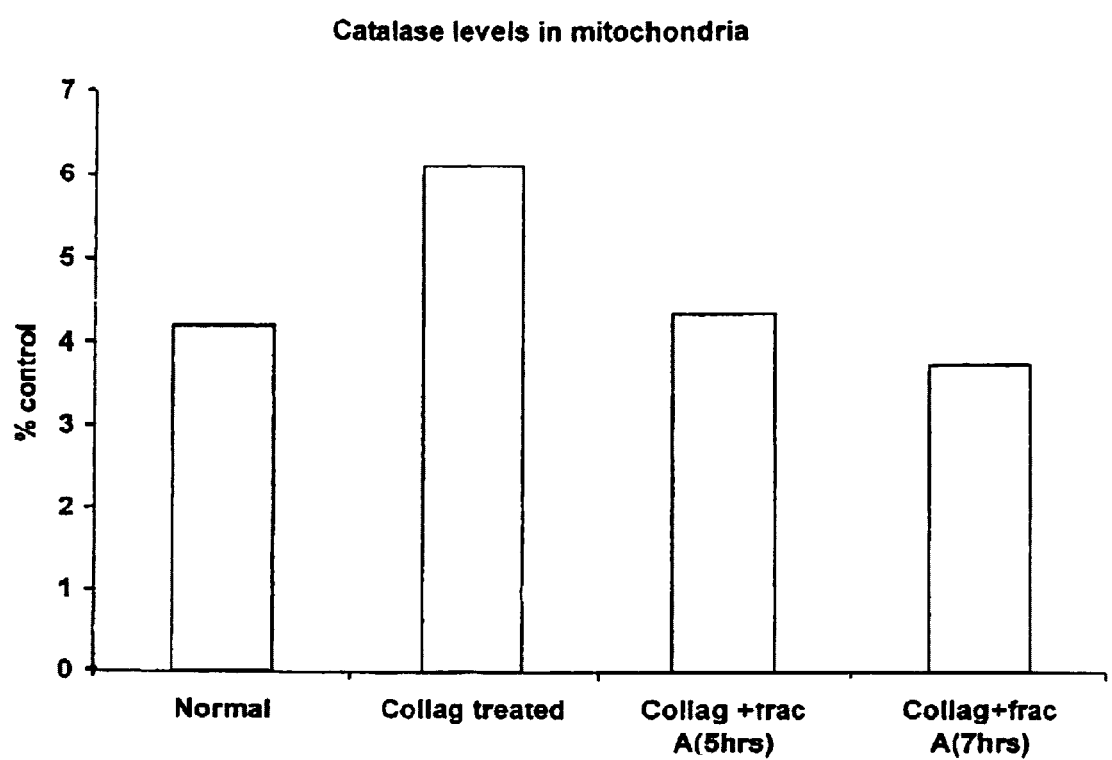
FIG. 6 shows Catalase levels in mitochondria after using fraction A and fraction B.

Catalase: This enzyme is reported to be present in minute amount in brain (FIG. 6)

Figure 7:
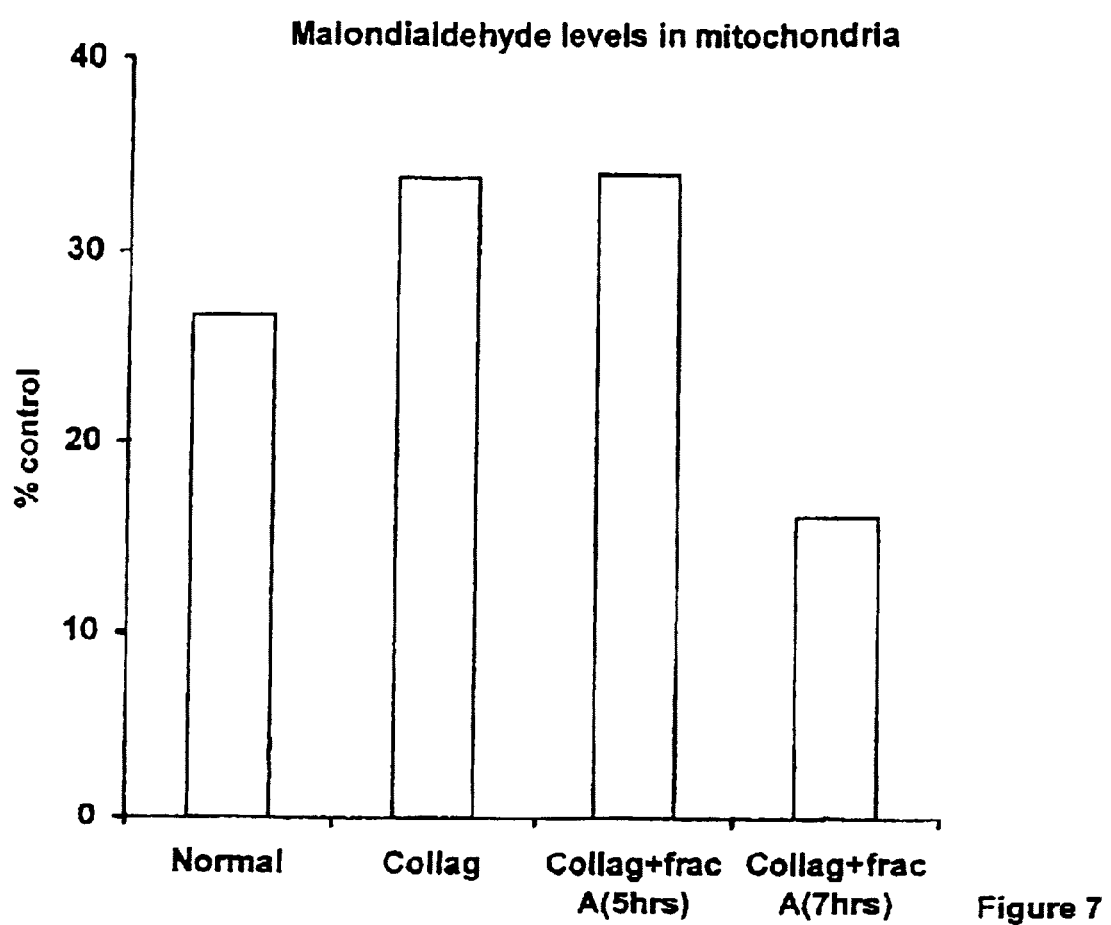
FIG. 7 shows Malondialdehyde levels in mitochondria after using fraction A.

TBARS: At 5 hours post collagenase treatment, the values were close to that of collagenase treated animals, while at 7 hours the values were decreased significantly as compared to the normal group indicating the anti-oxidant property of the test compound-fraction A (FIG. 7).

Mitochondria were isolated as described in Example 2.

Example 4

Adult male rats (250–350 gm.) from the C.D.R.I. Animal house were anaesthetized with 30 mg./kg. Pentobarbitone sodium. Jugular veins of the rats were exposed. Five drops of 10% formalin in 65% methanol was dropped on the vein. Six hours were allowed for thrombus formation which was then graded according to its presence or absence. [Blake O. R., Ashwin J. G., Jaques L. B.,; An assay for the antithrombotic activity of anticoagulants: J. Clin. Pathol., 12,118 (1959)]. Fraction A (ar-d-turmerone and turmerones) was given 200 µl.i.p./300 gm.rat in the treated group,while the untreated (control) group received equivalent amount of saline (i.p).

Result

The thrombus in the untreated group was 2.8 mg. and in the treated group it was 0.75 mg. showing an increase of 373.33% in untreated versus treated group.

Example 5

Rats were made hypertensive according to Goldblatt et. al. [Goldblatt H., Lynch J., Hanezal R. F., Serville W. W.: Studies on experimental hypertension,: The production of persistent elevation of systolic blood pressure by means of renal ischaemia J Exp Med; 59: 347–379 (1934)]. Eight weeks later the hypertensive rats had an average initial blood pressure of 200 mm/H g. After *Curcuma* oil, 683.65 mg./kg. was administered intraperitoneally the blood pressure fell to 115 mm/Hg in 15 min. and stayed at that level for more than 60 min.

TABLE 1

| Rats | Dose (i.p.) (683.65 mg/kg). | Blood Pressure Fall (%) | Duration (min.) | No. of Expt. |
|---|---|---|---|---|
| Hypertensive |  | 38.76 ± 7.19 | >60 min. | n = 3 |
| Normotensive |  | No fall | — | n = 2 |

Result

The compound lowers the blood pressure significantly in hypertensive rats and not in the normotensive rats. It reduces blood pressure without bradycardia due to β-adrenergic receptor antagonism or reflex tachycardia common to vasodilator [Nichols A. J, Gallai M. Ruffolo R. P Jr. Studies on the mechanism of arterial vasodilation produced by the noval antihypertensive agent. Carvediolol. Fundam. Clin. Pharmacol., 5: 25–38 (1991)].

Example 6

Figure 8:
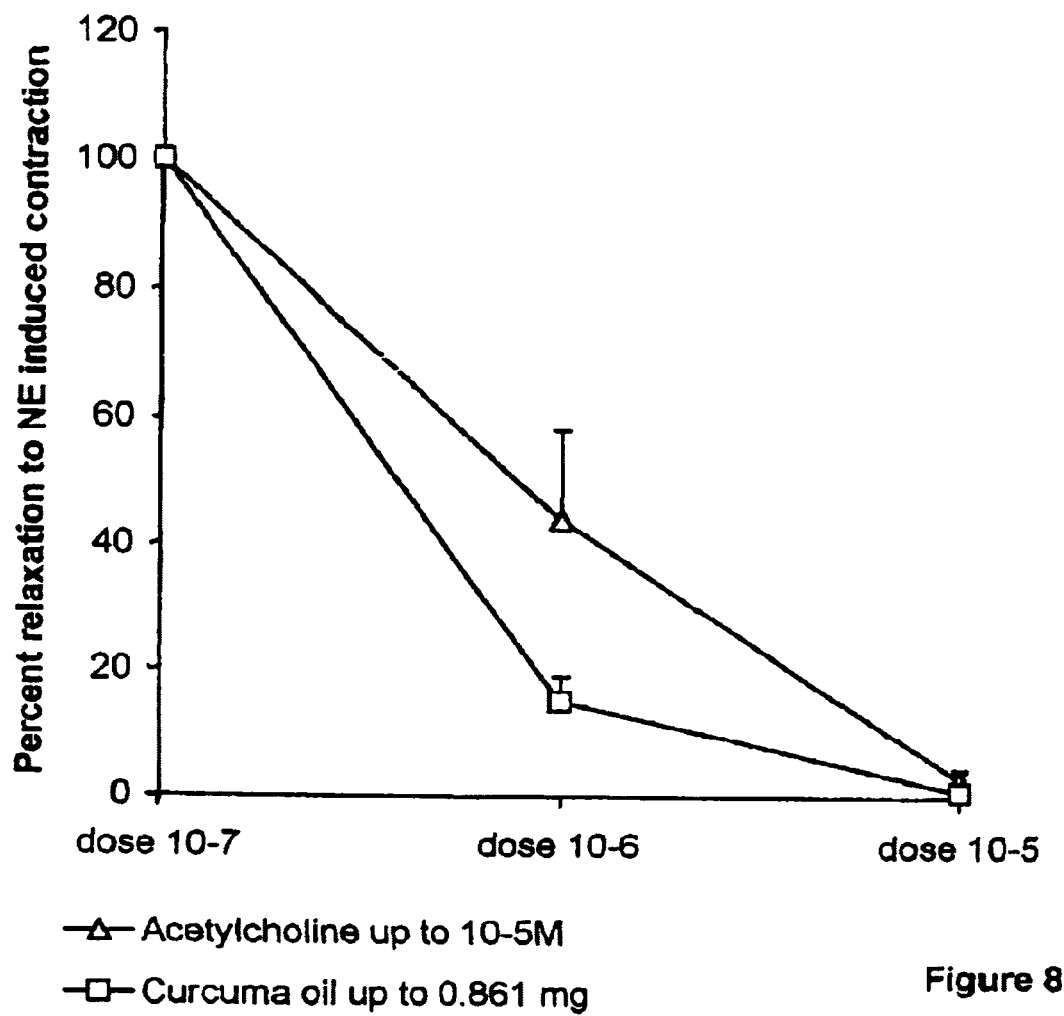
FIG. 8 shows change in percent relaxation to NE induced contraction.

Abdominal aorta was mounted according to Wolf gang et. al. [Wolf gang Auch-Schwelk, Zvonimir S. Katusic and Paul M. Vanhoutte: contractions to oxygen derived free radicals are augmented in aorta of the spontaneously hypertensive rats., Hypertension, 13, 859–864(1989)]. Aortic rings were contracted with norepinephrine $10^{-8}$ to $10^{-5}$ M. The contracted vessels were relaxed by acetylcholine or *Curcuma* oil, added in a stepwise manner. Acetylcholine was added in a concentration of $10^{-7}$ to $10^{-5}$ M. For *Curcuma* oil, the final contraction achieved was 0.861 mg in a 8 ml bath (FIG. 8). Protein Kinase C activator, Phorbol 12-Myristate 13-Acetate (PMA) ($10^{-7}$ M) induced contraction in the intact and denuded aortic strip preparation. Pretreatment with *Curcuma* oil, 0.881 mg. completely inhibited PMA induced contraction. It inhibits protein kinase C [Kaczmarck L. K.; The role of Protein Kinase C in regulation of ion channels and neurotransmitter release: Trends in Neurosciences, 10, 30–34 (1987); Jin-Moo Lee, Grabb M. C., Zipfel G. J., Choi D. W., J. Clin. Invest., 106, (6), 723–731(2000).

Result

*Curcuma* oil and acetylcholine caused complete relaxation in norepinephrine induced contraction showing a significant vasorelaxant effect.

Example 7

Nitric Oxide (NO) Scavenging by Test Compounds/Agents

Sodium nitroprusside (SNP) generates Nitric oxide (NO) [Sreejayan and Rao M. N. A: Nitric oxide scavenging by curcuminoids, J. Pharm. Pharmacol., 49, 105–107(1997)]. fraction-A, 86.14 mg was mixed in phosphate-buffer saline at different concentration of SNP (5–40 mM) Griess reagent in 1:1 ratio was mixed with the test compound (fraction-A). The absorbance of the above chromophore buffer formed with SNP, test compound (fraction-A) and Griess reagent was read at 546 nm and refer to the absorbance of standard solution of potassium nitrite treated in the same way with Griess reagent (Green L. C, Wagner D. A., Glogowski J, Skipper P. L., Wishnok J, S., Tannenbaum S. R., Analysis of nitrate, nitrite and $^{15}$N in biolo gical fluids; Anal. Biochem. 126, 131(1982). Marcocci L., Maguire J. J, Droy-Lefaix M. T., Packer L.: The nitric oxide scavenging property of Ginkgo biloba extract EGb 761, Biochem. Biophys. Res. Commun. 201,748 (1994).

Results

Figure 9:
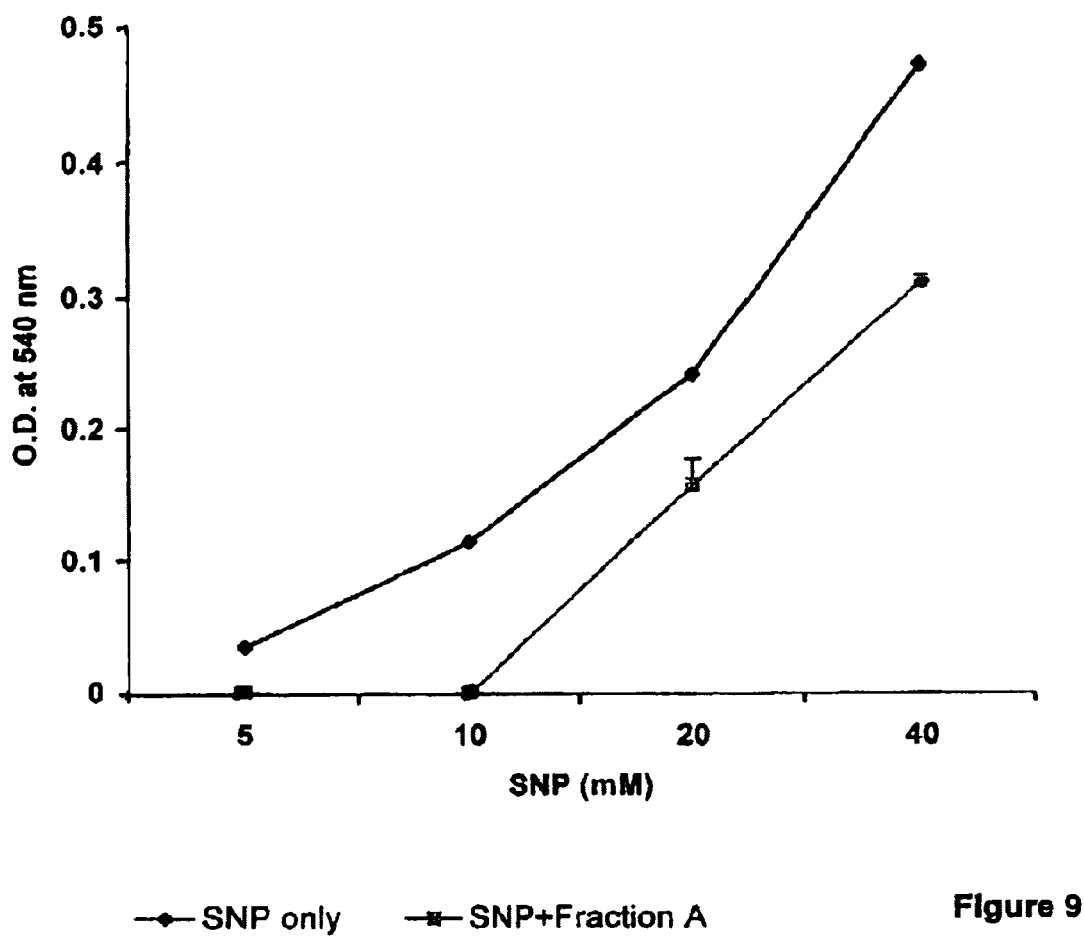
FIG. 9 shows change in SNP levels in mitochondria after using fraction A.

SNP generates nitric oxide and test compound (fraction A) scavenges the nitric oxide thus generated. The result indicated the test compound (fraction A) in focal ischaemia to be a scavenger of nitric oxide (FIG. 9).

What is claimed is:

1. A method for obtaining a lipid soluble extract from rhizomes and leaves of *Curcuma* species of the Zingiberaceae family and fractions of the lipid soluble extract, said method comprising the steps of:
   a) powdering the rhizomes and leaves of the *Curcuma* species to obtain a powder;
   b) extracting the powder with a polar organic solvent selected from the group consisting of alcohol and acetone under continuous stirring or sonication for about 24 hours at room temperature;
   c) repeating step b) two to five times.
   d) removing the polar organic solvent by distillation under reduced pressure and below 45° C. to obtain a concentrate;
   e) triturating the concentrate with a non-polar solvent selected from the group consisting of light petroleum and toluene;
   f) removing the non-polar solvent by distillation under reduced pressure and below 45° C. to obtain the lipid soluble extract;
   g) fractionating the lipid soluble extract using silica gel column chromatography using n-hexane, n-hexane:ethyl acetate mixture in a ratio of 95:5, and ethyl acetate as eluents which are used successively to obtain fraction A, fraction B, and fraction C, and
   j) fractionating each of fractions A, fraction B, and C further using HPLC or GLC to obtain the constituents of fractions A, B and C wherein the constituents of fraction A are selected from the group consisting of ar-turmerone of formula 1 and turmerone of formula 2; constituents of fraction B are selected from the group consisting of curcumene and zingiberine and constituents of fraction C are selected from the group consisting of germacrone, curcumerone, zedoarone, sedoarondiol, isozdedoaronidiol and curlone.

2. The method as claimed in claim 1, wherein fraction A constitutes about 75% by weight of the lipid soluble extract.

3. The method as claimed in claim 1, wherein ar-tumerone constitutes 95% of the fraction A.

4. The method as claimed in claim 1, wherein the pressure in steps d) and f) ranges between 7 and 11 mmHg.

5. A method for obtaining a lipid soluble extract from rhizomes and leaves of *Curcuma* species of the Zingiberaceae family, said method comprising the steps of:
   a) powdering the rhizomes and leaves of the *Curcuma* species to obtain a powder;
   b) extracting the powder with a polar organic solvent selected from the group consisting of acetone and alcohol under continuous stirring or sonication for about 24 hours at room temperature;
   c) repeating step b) two to five times,
   d) removing the polar organic solvent by distillation under reduced pressure and below 45° C. to obtain a concentrate;
   e) triturating the concentrate with a non-polar solvent selected from the group consisting of light potroleum and toluene; and
   f) removing the non-polar solvent by distillation under reduced pressure and below 45° C. to obtain the lipid soluble extract.

6. A method for fractionating the lipid soluble extract prepared by the method of claim 5, comprising the steps of
   a) fractionating the lipid soluble extract using silica gel column chromatography using n-hexane, n-hexane:ethyl acetate mixture in a ratio of 95:5, and ethyl acetate as eluents which are used successively to obtain fraction A, fraction B, and fraction C, and
   b) fractionating each of fractions A, fraction B, and C further using HPLC or GLC to obtain the constituents of fractions A, B and C wherein the constituents of fraction A are selected from the group consisting of ar-turmerone of formula 1 and turmerone of formula 2; constituents of fraction B are selected from the group consisting of curcumene and zingiberine and constituents of fraction C are selected from the group consisting of germacrone, curcumerone, zedoarone, sedoarondiol, isozdedoaronidiol and curlone.

7. The method as claimed in claim 6, wherein fraction A constitutes about 75% by weight of the lipid soluble extract.

8. The method as claimed in claim 6, wherein ar-tumerone constitutes 95% of the fraction A.

* * * * *